United States Patent [19]

Brenneman

[11] Patent Number: 5,114,862

[45] Date of Patent: May 19, 1992

[54] METHOD FOR DISTRIBUTING AND ANALYZING A FLUID SAMPLE ONTO A TEST SURFACE

[75] Inventor: Allen J. Brenneman, Elkhart, Ind.

[73] Assignee: Miles Inc., Elkhart, Ind.

[21] Appl. No.: 693,155

[22] Filed: Apr. 29, 1991

Related U.S. Application Data

[62] Division of Ser. No. 351,489, May 15, 1989.

[51] Int. Cl.$^5$ .............................................. G01N 1/10
[52] U.S. Cl. .................................. 436/169; 436/170; 436/171; 436/180
[58] Field of Search ...................... 422/56, 57, 58, 100; 436/169, 170, 180, 174

[56] References Cited

U.S. PATENT DOCUMENTS

| | | | |
|---|---|---|---|
| 4,248,973 | 2/1981 | Kallies | 422/58 |
| 4,447,546 | 5/1984 | Hirschfeld | 436/527 |

Primary Examiner—David L. Lacey
Assistant Examiner—Thomas E. Daley
Attorney, Agent, or Firm—Roger N. Coe

[57] ABSTRACT

A reagent format having an inverse funnel shaped body which includes a central capillary tube that opens into a flow passageway. The flow passageway is formed, in part, by providing a recessed flow surface at one end of the inverse funnel shaped body which is surrounded by a stepped shoulder. A test substrate, such as reagent film, is secured to the shoulder so as to form one surface of the flow passageway. The device is suitable for both drawing and spreading a fluid test sample onto a test substrate in one step. Additionally, one or more small diameter vent passageways open into the flow passage to allow for air to escape when fluid is drawn into the flow passage through capillary action. The pen-shaped body is also formed of a clear or translucent material such that the flow of the test fluid can be observed by the user.

2 Claims, 4 Drawing Sheets

METHOD FOR DISTRIBUTING AND ANALYZING A FLUID SAMPLE ONTO A TEST SURFACE

This is a division of application Ser. No. 351,489, filed on May 15, 1989.

BACKGROUND OF THE INVENTION

1. Field of the Invention

The present invention relates to a device and method for distributing a liquid sample onto a test surface. More particularly, the present invention relates to a reagent format which draws and distributes fluid over a testing area by capillary action.

2. Description of Related Art

Many different designs of test apparatus which involve chemical analysis of liquids such as water, milk, as well as biological fluids including blood and urine are known in the art. Some of these testing apparatus are suitable for liquid analysis, wherein there is required the addition of a liquid reagent for analysis of a substance termed an "analyte". The reagent, upon contacting a liquid test sample containing the analyte, affects formation of a colored material or other detectable change in response to the presence of the analyte. Other systems depend on a dry system, such as pH papers and the like, where the paper or other highly absorbent carrier is impregnated with a material which is chemically reactive or responsive when placed in contact with the liquid containing the analyte. The response or reaction generates a color change or other type of detectable change. Depending to a great extent upon the selection of responsive material, the change is usually qualitative or at best semi-quantitative.

For diagnostic chemical analysis wherein the testing of biological fluids such as blood, plasma, urine and the like are utilized, it is preferable to produce highly quantitative results rapidly, conveniently and with assurance of accurate results. Also, it is desirable to have precise control and monitoring of the liquid specimen that is being subjected to the test. The ability to precisely control and monitor the liquid specimen is particularly important in tests involving machine reading of the reaction. In analysis involving machine reading it is important to have the reading machine begin its analysis at the appropriate time. In addition, when relying on machine readings, it is important that a calibrated amount of the test specimen be exposed to the test substrate so that the proper reaction will take place and any interference with optical detection or other detection of color changes is avoided.

A variety of devices and methods are relied upon in presenting the test liquid containing the analyte to the surface of the substrate. Many dry chemistry reagents have the liquid test sample placed upon the test substrate surface and then spread by the user. The application of the liquid test sample volume and the spreading thereof is user variable and influences the performance of the reagent. In addition, such user contact is undesirable from the standpoint of increasing the chance of user contamination—especially when dealing with body fluids such as blood or plasma.

In U.S. Pat. No. 4,776,904 there appears discussion focusing on reagent films which represent one form of the test substrates described above.

Additional testing devices utilizing dry chemistry reagents include devices such as those disclosed in U.S. Pat. Nos. 4,647,430; 3,814,668 and 3,215,855 where the testing device is dipped into the fluid. These devices, however, are not suitable for many test requirements due to the drawbacks of requiring large volumes of liquid test samples as well as the increased likelihood of contamination brought about by the need for wiping off excess fluid to avoid dripping.

The ONE TOUCH (TM) by Lifescan presents a reagent format wherein a drop of blood is placed on an exposed surface of a reagent film and the results are viewed from the other side of the film. The sample is introduced by having the user transfer the sample from the fluid sample source to the exposed film surface. The amount and distribution of the fluid sample is user variable and thus difficult to control.

A variety of devices and methods have been developed for transporting liquid in a controlled and predetermined flow pattern. Many of these items have been concerned with uncontrolled and undirected capillary flow of the liquid across surfaces. Some problems that have been encountered with uncontrolled flow include formation of trapped air pockets and incomplete wetting of certain portions of the surface. Air pockets create problems when the test device is examined through a microscope or by way of automatic methods because the examination of the liquid and/or wetted surfaces results in different test data being collected. The examinations involving automated systems are based on a presumption of the presence of the liquid in the scanning area and therefore the absence of the liquid in the relevant scanning area will throw off the value of the reading and will give an unreliable result. The problem of air pockets is a common occurrence particularly when dealing with configurations which have sharp corners and synthetic resin surfaces which are generally hydrophobic.

A variety of different types of liquid transport devices have been developed in the prior art including that shown in U.S. Pat. No. 4,761,381 to Blatt et al. Also, in Columbus, U.S. Pat. No. 4,233,029 there is described a device containing a means for directing capillary flow along predetermined paths by use of grooves in the opposed surfaces of a capillary chamber.

Another configuration for the transport of a liquid test specimen is shown in Columbus, U.S. Pat. No. 4,254,083, which provides for an exterior drop receiving surface containing a particular opening configuration which is intended to facilitate the centering of the drop.

Buissiere et al., U.S. Pat. No. 3,690,836, describes a device consisting of a capillary space between two plastic sheets which are sealed in a continuous perimeter and which enclose an uncompressed absorbent material which fills the capillary space. At least one opening at the top sheet provides for access to the reaction chamber.

A liquid transport device which provides for diversion of capillary flow into a second zone is shown in Columbus, U.S. Pat. No. 4,473,457. The device has two pathways for flow of the specimen and permits the introduction of two different specimens through two apertures. The two liquids then will flow towards and into a common area. The configuration of the structure of Columbus permits potentiometric determinations to be made. See also Columbus, U.S. Pat. No. 4,302,313, which shows a device suitable for potentiometric analysis of liquid ions. Special grooved surfaces under the member 36 are said to control capillary flow.

Another device is shown by Columbus, U.S. Pat. No. 4,271,119, which has a downstream diverting aperture in a wall member of a first capillary zone which provides capillary flow into a second capillary zone extending from that wall member.

The aforementioned liquid transport devices rely on the placement of a fluid test sample within an access aperture before the capillary action can induce Again, the reliance on user insertion of the fluid sample into the access aperture means that there will be a subjective determination as to how much fluid to insert into the access aperture. Such subjective determination as to the appropriate volume of fluid is often too high thus necessitating an overflow device or subsequent wiping off of the device surface. Moreover, when the inserted volume of fluid is insufficient, repeated insertions often result in the last insert exceeding the desired volume which again leads to an overflow. Further, the need for an overflow chamber and/or wiping off of the surface is an indication that the volume of fluid test material is not being efficiently utilized.

Additionally, even with the liquid transport systems, evaporative cooling presents a problem in precision testing. There is also present in the prior art the problem of not obtaining a sufficient amount of sample on the test substrate due to difficulty in determining or detecting when the test substrate is sufficiently covered.

SUMMARY OF THE INVENTION

The present invention is directed at solving, inter alia, the aforementioned problems associated with the prior art. For example, the present invention provides a device which is easy to fill in a one step process, requires a small testing fluid volume, and gives a visual feedback to the user that the format is filled with the appropriate amount of testing fluid. The design of the present invention allows for the drawing of the testing fluid and the spreading of a uniform and uninterrupted layer of the testing fluid over the test substrate all in one step. In addition, the invention is adapted to totally contain the volume of the testing fluid and also minimize the evaporative cooling of the testing fluid. The invention also avoids blotting, wiping, or removal of the testing fluid by the user. Moreover, the invention is adapted for use with a reagent film that is easily read from the side opposite to which the sample is applied.

The present invention is also well suited for use with testing instruments such as reading machines and the like. An instrument utilizing the present invention would not be dependent upon the user to control the timing since the present invention can be loaded into the instrument prior to filling and an optical system would be able to sense when the required fluid flow is present. Also, whether relying on visual inspection or a reading machine, the structural arrangement of the present invention provides for easy detection of when a sufficient sample has been obtained as well as the color change taking place in the test substrate.

In achieving the above advantages over the prior art, the present invention provides a disposable capillary tube device that includes a main body of solid material having a neck portion with a relatively wider base portion so as to provide the disposable capillary tube device with an inverse funnel shape. A through-hole extends centrally through the neck portion and the base so as to form openings in each end and a capillary tube therebetween. The opening at the base end includes a recessed flow surface surrounded by a stepped shoulder.

In a preferred embodiment, there also exists a deeper recess positioned between the outer edge of the flow surface and the stepped shoulder which assists in creating a uniform flow over the flow surface. In addition, a vent passageway extends from the deeper recess, through the interior of the main body, and out to the exterior of the main body.

The main body of the device is preferably formed of a clear or translucent solid plastic such as polycarbonate, acrylic, or polystyrene. Furthermore, the formation of the capillary tube and the vent passageway (or passageways) can be achieved, for example, by pre-forming in a molding process or a subsequent machining process. The through-hole and vent passageways are formed so as to minimize evaporative cooling and the two represent the total amount of exposed area when the reagent film or testing substrate is in place.

In a preferred embodiment of the present invention the through-hole representing the capillary tube generally has a diameter of about 0.02 to 0.04 inches. Additionally, the vent passageway is of a lesser diameter than the capillary tube generally ranging between about 0.01 to 0.03 inches. Consequently, the total fluid exposure area is kept minimal and the fluid within the device is not subject to undue evaporative cooling. The diameter of the capillary and vent passageway must, however, be of a large enough diameter to be moldable if molding is the desired method of manufacture. Therefore, there is a trade off between making the vent passageway and capillary tube of a large enough diameter to be moldable and small enough to minimize both blood volume and exposed surface area. In the prior art situations where a 0.2 inch by 0.2 inch reagent pad is relied upon, there is an exposed area of 0.04 square inches. Thus, the present invention provides the possibility of substantially reducing (e.g. by a factor of 25) the exposed surface area.

The stepped shoulder of the present invention provides a location to which a test substrate such as a reagent film can be attached. By utilizing a test substrate which covers over the entire flow surface at the second end of the main body, it is possible to create an essentially sealed flow passageway. The test substrate is preferably attached to the stepped shoulder of the main body by an adhesive or by sonic welding.

In another preferred embodiment of the present invention, rather than directly attaching the test substrate to the stepped shoulder, a molded ring, having the test substrate attached to it, is releasably secured to the base end of the main body. The vent passageways are formed by providing one or more grooves in the exterior surface of the main body such that, when the mold ring is secured to the main body and positioned such as to cover a portion of the groove(s), a sealed passageway is provided. The formation of grooves on the exterior surface avoids any difficulty in having to form narrow vent passageways in the main body.

A preferred shape of the present invention is an inverse funnel shape which includes a top, relatively narrow neck portion, a conical mid-region and a cylindrical base portion. With this arrangement, the application of the device to the fluid testing volume and the spreading of that fluid are both achieved in one step. Thus, for example, in analyzing a quantity of blood obtained by sticking a patient's finger with lance or needle such as a GLUCOLET, (TM) the tip of the capillary tube is placed in contact with the volume of blood. Capillary action then fills the tube and spreads the blood across the reagent surface in the flow passageway formed between an inside surface of the reagent film and the flow surface of the main body. As the fluid flows a venting of air contained within the main body occurs through the vent passageways When the device is filled the flow stops and the color development of the reagent takes place.

The use of a narrow neck portion and a conical midregion enhances visual detection. If not enough blood has been applied only the capillary tube (i.e., throughhole) diameter appears red to the user. However, when enough blood has been introduced, the entire flow surface appears red and the device is then "read" from the non-attached side of the reagent film. If an optic system is being relied upon, timing of the read time is started when the optics system senses a start of color change.

Other features and advantages will become apparent upon reference to the following Description of the Preferred Embodiments and drawings.

DESCRIPTION OF THE PREFERRED EMBODIMENTS

Figure 1A:
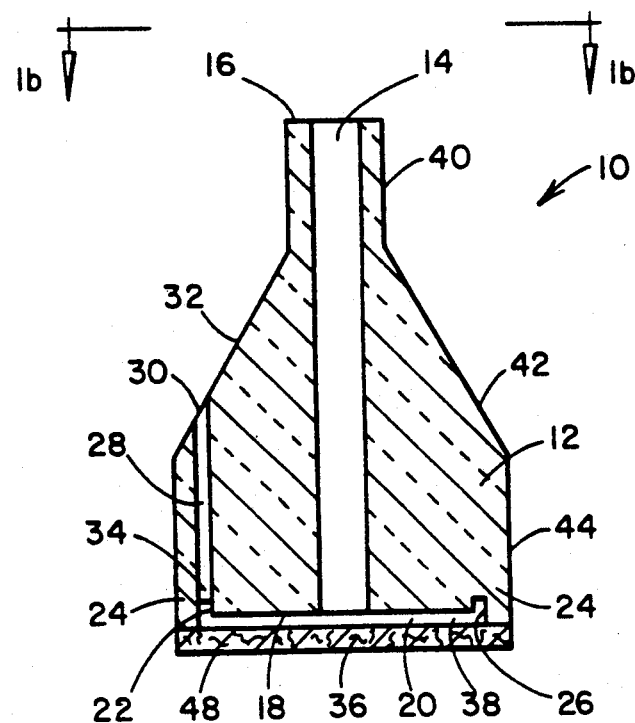
FIG. 1A is an elevational sectional view of a preferred embodiment of the present invention.
Figure 1B:
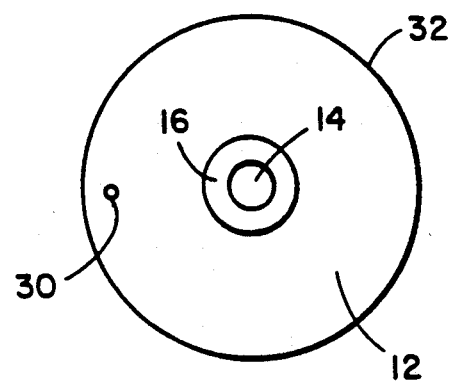
FIG. 1B is a plan view of the embodiment shown in FIG. 1A.

FIGS. 1A and 1B show an elevational sectional view and a plan view, respectively, of a preferred embodiment of the present invention. In FIGS. 1A and 1B, a device 10 is shown to include a main body 12 having a through-hole 14 extending along its length so as to form a capillary tube. Throughhole 14 extends from a first end 16 of main body 12 to a second end 18 of main body 12.

At the second end 18 of main body 12 is located flow surface 20 shown to extend outwardly away from the opening of through-hole 14. Flow surface 20 is illustrated as being essentially planar. Moreover, flow surface 20 is shown to have an outer edge 22. Spaced outwardly from, and surrounding the outer edge 22, is stepped shoulder 24. Between the outer edge 22 and stepped shoulder 24 is formed recess 26 which includes as one of its sides outer edge 22. Recess 26 extends uninterrupted about the periphery of the flow surface 20.

Extending through the interior of the main body 12 is vent passageway 28. Vent passageway 28 includes a first outlet 30 formed in the exterior 32 of main body 12. The other outlet 34 of vent passageway 28 opens into recess 26 and the flow surface 20. In the embodiment shown in FIG. 1 only a single vent is illustrated; further vent passageways are also possible, but the number and size are preferably kept to a minimum to avoid evaporative cooling. In addition, recess 26 provides a means to ensure that the fluid sample spreads evenly in all direction over flow surface 20. In utilizing a single vent passageway the fluid sample would have a tendency to be drawn to the single vent passageway area. However, recess 26 creates a peripheral cavity which acts to evenly draw the fluid out away from the capillary tube opening.

Figure 2:
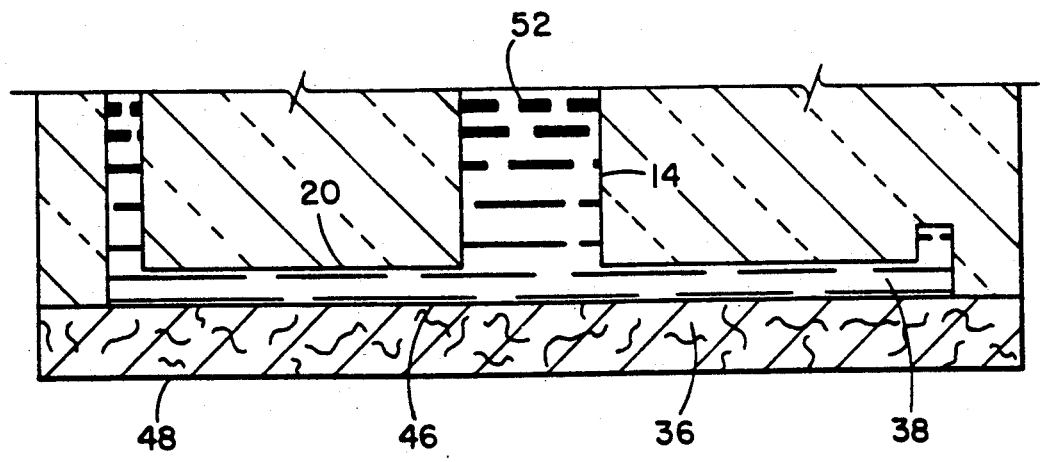
FIG. 2 is an enlarged cut-away view of the embodiment shown in FIG. 1A.

Secured to the end of stepped shoulder 24 is test substrate 36 which is shown in FIG. 2 to be a reagent film. Test substrate 36 is secured to the shoulder 24 by any suitable manner such as adhesion or sonic welding. Positioning test substrate 36 in such a manner acts to create flow passageway 38 which is in communication with the opening of the second end formed by the through-hole 14.

Main boy 12 is preferably formed of a clear or translucent plastic such as polycarbonate, acrylic, or polystyrene. Further, main body 12 is formed in an inverse funnel shape with a neck region 40, a transition region 42, and a base region 44. The arrangement of neck region 40 and transition region 42 provides for enhanced viewer detection. When fluid enters flow passageway 38, transition region 42 vividly displays, much like an LED light, the presence of a colored fluid. The shape of main body 12 can be formed, for example, in a molding process (e.g. injection molding), a machining process, or the like. Furthermore, through-hole 14, flow surface 20, recess 26 and vent 28 can be formed during the molding process or in a subsequent machining process. Various other configurations would also be possible including entirely cylindrical and multi-sided shapes. Nonetheless, in addition to the visual detection advantages brought about by the shape of neck region 40 and transition region 42, the embodiment illustrated in FIG. 1A depicts a shape which is well suited for manipulation by the user.

Main body 12 preferably has a total length (from the first end 16 to the free edge of shoulder 24) of about 0.25 to 0.38 of an inch. Moreover, the neck region 40 preferably has an external cross-sectional diameter of about 0.07 to 0.11 and, more preferably, about 0.09 of an inch. The external cross-sectional area of the base 44 is contemplated to be about 0.2 to 0.4 and, more preferably, about 0.25 of an inch. The capillary tube 14 preferably has a diameter of about 0.02 to 0.04 and, more preferably, about 0.035 of an inch. The distance the flow surface 20 extends outwardly away from the capillary opening is contemplated to be about 0.18 to 0.24 of an inch and, more preferably, about 0.220 of an inch.

Also, the gap formed between the inside surface 46 of test substrate 38 and the flow surface 20 is preferably about 0.003 to 0.010 and, more preferably, about 0.007 of an inch. Each vent passageway preferably has a diameter of about 0.01 and structural arrangement of the present invention thus only requires less than about 10 microliters of fluid.

As illustrated in FIG. 2, test substrate 36 can include a reagent film. In a preferred embodiment the reagent film is of a type which allows for a bottom read; that is, an evaluation can be achieved by an inspection of the outside surface 48 (FIG. 2) of the reagent film. FIG. 2 further reveals testing fluid 52 filling up flow passageway 38 as well as a portion of capillary tube 14

A typical reagent film includes multiple layers with an absorbent carrier impregnated with one or more reagents, typically including a color former. Over the absorbent layer is often positioned a semipermeable membrane which allows the analyte to pass through but prevents passage and absorption of certain interfering components that could impair the test results. Integral analytical elements adapted for automated test procedures are discussed in U.S. Pat. Nos. 3,368,872 and 3,526,480.

As is evident from the above discussion, the preferred size of main body 12 is relatively small. In view of this the invention is designed for possible use with a holding instrument.

Figure 3:
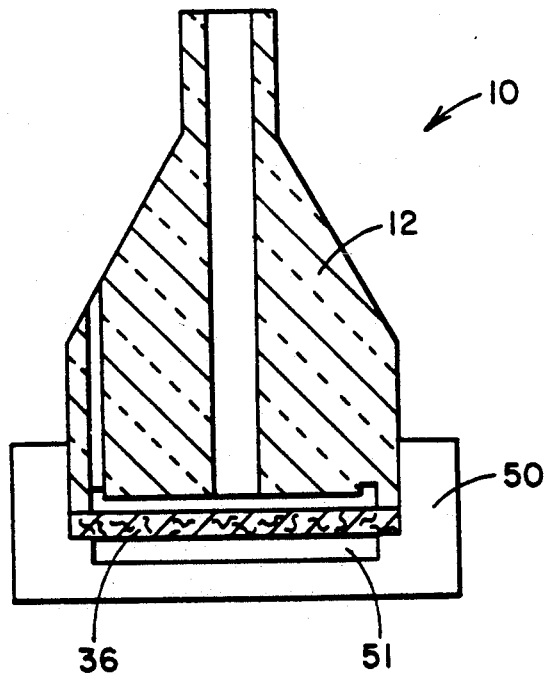
FIG. 3 schematically illustrates a reading instrument attached to the present invention.

In FIG. 3 is illustrated a reading instrument 50 into which the device 10 may be inserted prior to or after use. Hence, it is possible for reading instrument 50 to double as a holding instrument. Reading instrument 50 may include an optical system 51 suitable for an evaluation of the changes occurring in test substrate 36 upon contact with the fluid analyte. It is also contemplated that optical system 51 include a timing device (not shown) which is started when the optics system senses a color change in the test substrate.

Figure 5:
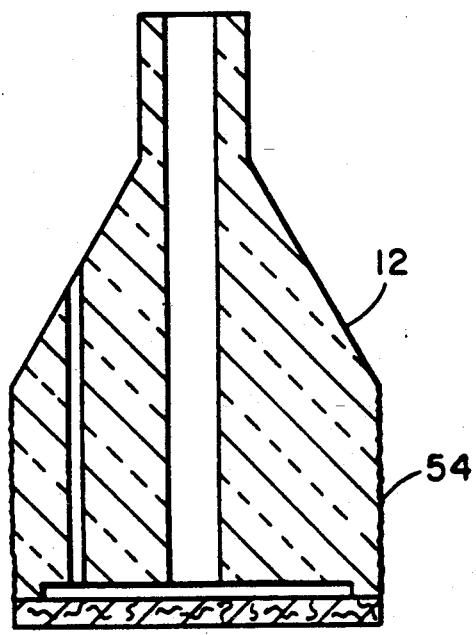
FIG. 5 depicts a holding instrument for use with the present invention.
Figure 5:
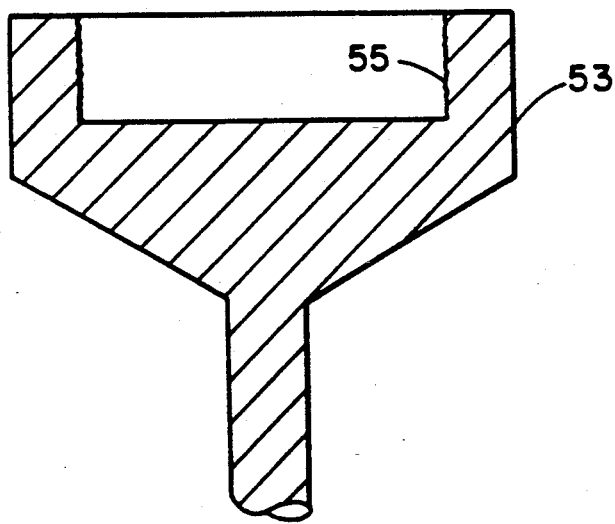

Various other holding instruments are also contemplated for use with the present invention. FIG. 5 illustrates a holding instrument 53 for use with the present invention. FIG. 5 shows main body 12 having roughened exterior portion 54 which is adapted for a frictional fit with roughened holder surface 55 of handle 51. Other arrangements contemplated include arrangements such as a snap fit, force fit or threaded engagement.

In operation, end 16 of device 10, either with or without instrument 50 or instrument 53 attached, is placed in contact with a volume of test fluid such that the capillary structure of device 10 acts to draw fluid along capillary tube 14. Capillary action causes the fluid to fill the tube 14 and eventually flow into passageway 38. The volume of air is vented through the vent passageway 28 or passageways. The size of the vent passageway or passageways is such that evaporative cooling is minimized. Also, the size of the vent passageway(s) restricts the fluid from passing out through the exterior of the main body. The restrictive nature of the vent passageways is also able to maintain the air within the main body at a pressure which helps to prevent the formation of air bubbles within the testing fluid. In other words, the pressure created by the fluid within the capillary is confronted by the pressure of the air such that air bubble avoidance in the fluid within the flow passageway is made possible.

Due to the structural arrangement of the present invention and the use of a transparent or translucent material for the main body, the user can visually observe (especially when blood is the test fluid) when the test fluid flows from the capillary tube 14 across the reagent format or test substrate 36. When the test fluid has not entered the flow passageway, the user will observe that only the capillary tube diameter appears colored. If, however, a sufficient volume of test fluid has filled the flow passageway the user will be able to observe a color change over the entire flow surface. Hence, the user can easily detect when a sufficient volume of testing fluid has been provided and discontinue the flow simply by terminating the capillary action. A termination of the capillary flow is brought about by a simple withdrawal of the tip or end 16 from the fluid source.

The structural arrangement of device 10 avoids the problem of wiping off excess fluid and the problem of contamination as the test fluid in device 10 is contained entirely within the device and after use coagulation occurs and the fluid sample is contained entirely within the capillary flow passageways. Only the small surface area of the tip or end 16 of the device 10 is exposed to the test fluid. Tip 16 is shown in FIG. 1A to have a planar surface. Other surfaces are also contemplated including a convex or concave surface. Although capillary tube 14 is shown in FIG. 1A to be centered with vent passageway 28 extending parallel and to one side of capillary tube 14, it is also possible to position the capillary tube and vent in different positions such as both to one side of the center line of main body 12. The vent passageway 28 or capillary tube may also extend at an angle to the center line if convenient.

Figure 4A:
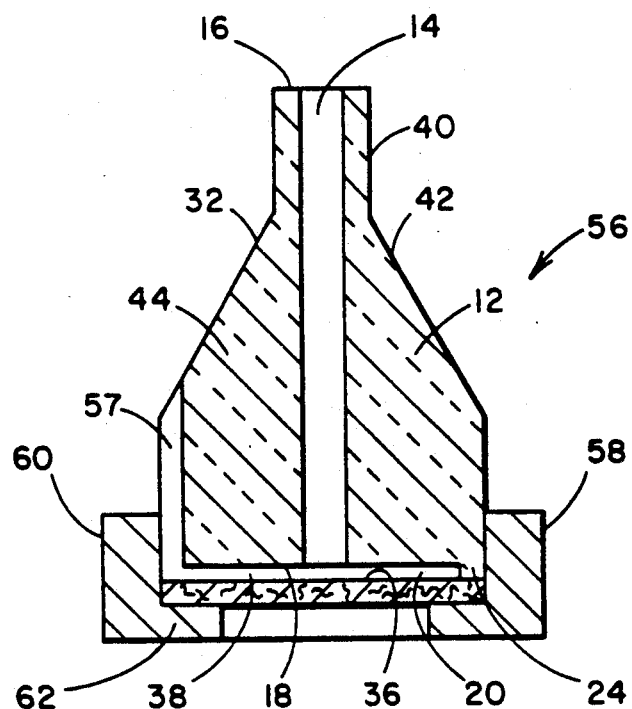
FIG. 4A is an elevational sectional view of another preferred embodiment of the present invention.
Figure 4B:
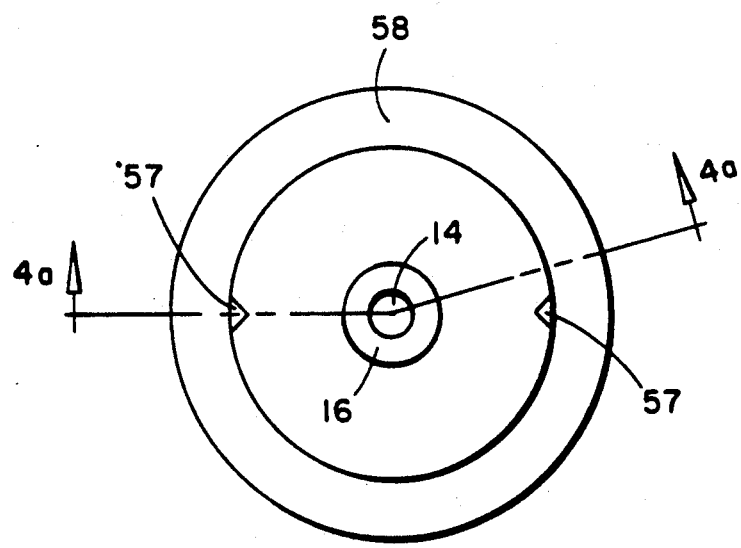
FIG. 4B is a plan view of the embodiment shown in FIG. 4A.

FIGS. 4A and 4B illustrate another preferred embodiment of the present invention. The device 56 includes many similar features as that of device 10. Those features in device 56 which are similar to device 10 are designated with corresponding dashed numbers. In device 56 rather than vent passageways being formed internally, grooves 57 are formed along the exterior surface 32' of main body 12'. The grooves 57 extend upwardly from, and are in communication with, the flow passageway 38' such that a capillary structure is provided.

Releasably secured to the base 44' of main body 12' is a test substrate support 58. Test substrate support 58 is shown in FIGS. 4A and 4B to include a vertical ring 60 extending peripherally about the base as well as horizontal ring 62 extending inwardly so as to cover a portion of second end 18'. A test substrate 36' is secured to holder 58 so as to come in sealing contact with stepped shoulder 24'. Holder 58 can be attached in any suitable manner including a snap fit, threaded attachment or friction fit.

The vent passageways 57 are completed when test substrate holder 58 is releasably secured to base 44'. In other words, the fit between holder 58 and base 44' is such that grooves 57 are covered so as to complete the formation of the vent passageways.

Rather than just two grooves 57 placed diametrically opposite to one another, the invention also contemplates, in some situations, the use of more than two grooves. When the fluid being tested is such that continuous and even flow over the entire flow surface requires more than two diametrically opposed grooves, it is possible to add additional equally spaced grooves. In addition, there is also contemplated a series of grooves placed end to end so as to form a serrated external surface in main body 12'. The effects of evaporative cooling must also be considered in determining the appropriate number of grooves to be formed in main body 12'.

Operation of device 56 is similar to that of device 10. Analysis of the color change in the test substrate is achieved either visually or with use of a reading instrument as previously described in the first embodiment.

Further modifications and variations of the invention will be apparent from the foregoing and are intended to be encompassed by the claims appended hereto.

What is claimed is:

1. A method for distributing and analyzing a fluid sample, comprising:

attaching a reagent film having a first surface and a second surface to a reagent format device comprising main body, said main body having a capillary tube extending from a first end of said main body through to a second end of said main body and forming an opening at each end, said second end including a flow surface surrounding the opening and extending outwardly to an outer edge of the main body, said second end further including a step shoulder extending peripherally about the outer edge of said flow surface to contain said reagent film, said main body further including a vent passageway having an outlet in communication with said flow surface;

moving said reagent format device into direct contact with a fluid sample such that said fluid sample is introduced into the first end of said capillary tube and flows into said flow surface where said fluid sample contacts the first surface of said reagent film; and thereafter analyzing any change in the color of the reagent film by viewing the second surface of said reagent film.

2. The method of claim 1 which further comprises the step of venting air initially contained within the capillary tube through the vent passageway.

* * * * *